United States Patent [19]

Schoggen et al.

[11] 4,252,761

[45] Feb. 24, 1981

[54] PROCESS FOR MAKING SPONTANEOUSLY DISPERSIBLE MODIFIED CELLULOSIC FIBER SHEETS

[75] Inventors: Howard L. Schoggen; John W. Smith, both of Memphis, Tenn.

[73] Assignee: The Buckeye Cellulose Corporation, Cincinnati, Ohio

[21] Appl. No.: 924,527

[22] Filed: Jul. 14, 1978

[51] Int. Cl.$^3$ .............................................. B29J 1/02
[52] U.S. Cl. .................................... 264/120; 264/121
[58] Field of Search ............................... 264/121, 120

[56] References Cited

U.S. PATENT DOCUMENTS

| 3,071,805 | 1/1963 | Merkle | 264/120 |
| 4,096,311 | 6/1978 | Pietreniak | 264/121 |
| 4,160,004 | 7/1979 | Curry et al. | 264/128 |

*Primary Examiner*—Donald E. Czaja
*Assistant Examiner*—James R. Hall
*Attorney, Agent, or Firm*—Monte D. Witte; Richard C. Witte; John V. Gorman

[57] ABSTRACT

Strong, low basis weight, spontaneously dispersible sheets of modified cellulosic fibers. The sheets are prepared from modified cellulosic fibers such as crosslinked carboxymethyl cellulose or essentially acidic sodium carboxymethyl cellulose. Mixtures of modified fibers with unmodified fibers are also disclosed. The process of preparing the sheets comprises the steps of airlaying the fibers to form an airfelt, increasing the moisture content of the airfelt, and compacting the moisturized airfelt.

12 Claims, No Drawings

PROCESS FOR MAKING SPONTANEOUSLY DISPERSIBLE MODIFIED CELLULOSIC FIBER SHEETS

BACKGROUND OF THE INVENTION

1. Technical Field

This invention relates to strong, low basis weight, spontaneously dispersible sheets comprising modified cellulosic fibers and to a process for producing such sheets.

2. Background Art

Numerous processes for making sheets of fibers are known in the art. The most common is, of course, the Fourdrinier process which is used extensively to make sheets of paper. Another papermaking process that has been widely recognized as being useful is that described by Sanford and Sisson in U.S. Pat. No. 3,301,746 issued Jan. 31, 1967. Sheets of paper made by any of the conventional papermaking processes or by the Sanford and Sisson process can and do exhibit wide variations in strength properties which can be closely controlled by those skilled in the art. While papers that tend to repulp on wetting can and have been made, strong sheets of fibers with truly spontaneous dispersibility in water and other liquids have been essentially unknown.

Airlaying fibers to form non-woven webs is well known in the art. These non-woven webs, which are known as airfelts and which find widespread use in a variety of products such as disposable diapers and the like, are absorbent, but are normally quite weak. These airfelts, in the absence of extraneous binders, do tend to repulp in water, but as before, lack spontaneous dispersibility.

Trokhan and Sisson in British Pat. No. 1,500,053, published Feb. 8, 1978, describe a process wherein fibers at a controlled moisture level of less than about 10% by weight of bone dry fiber are disintegrated, air laid, and compressed to form airfelts such as those used in diapers. These airfelts, as other air laid webs, lack strength and spontaneous dispersibility.

Burgeni in U.S. Pat. No. 3,017,304, issued Jan. 16, 1962, teaches a process in which an airfelt is moistened on at least one surface and then subjected to compressive forces. A paper-like skin is formed on the moistened surface. Since bonds in the skin are described as papermaking bonds, the fibers used must be those which will form bonds in the presence of moisture and pressure. From about 3% to about 13% moisture is sprayed onto the airfelt, on either one or both sides, immediately prior to subjecting the airfelt to compressive forces. Since the moisture is concentrated at the surface of the airfelt, the localized level of moisture is considerably higher than the average 3% to 13% noted. This process, then, approximates a conventional papermaking process in that fibers associated with relatively large amounts of water are brought close together by external forces and the excess water is then removed. In this particular case, the excess moisture ultimately diffuses throughout the pad thereby eliminating the necessity of deliberate drying. While this technique does increase the strength of airfelts, the strength increase is only moderate and the final products are not spontaneously dispersible in liquids. In fact, the presence of the paperlike skin on the surface of the airfelt tends to retard the normal repulping of the airfelt.

Schoggen, Holmgren and Harris in U.S. Pat. No. 3,826,711, issued July 30, 1974, describe an exemplary method of making sheets from modified cellulosic fibers. In this process, the fibers are deposited on a wire, such as a Fourdrinier wire, from a water-organic solvent slurry and then are subjected to treatment with alcohol to displace the water down to a level from about 2% to about 50% by weight prior to final drying. While the sheets of modified cellulosic fibers made by this process have a certain degree of strength, and while some of the sheets have spontaneous dispersibility if the proper modified cellulosic fibers are used, the basis weight of sheets formed by this process is of necessity relatively high. Further, the requirement of an organic solvent necessitates the use of relatively complex processing equipment which must contain solvent recovery sub-systems if it is to be economically and environmentally acceptable. Such equipment does not lend itself readily to locations other than those where the modified cellulosic are produced. That is to say, this excellent process is designed primarily for use as a step in the manufacturing process of modified cellulosic fibers.

SUMMARY OF THE INVENTION

Strong, low basis weight, spontaneously dispersible sheets comprising modified cellulosic fibers are prepared by airlaying the fibers to form an airfelt, increasing the moisture content of the airfelt, and compacting the moisturized airfelt.

It is an object of this invention to provide a strong, low basis weight, spontaneously dispersible sheet comprising modified cellulosic fibers.

It is a further object of this invention to provide sheets of paper comprising modified cellulosic fibers without the use of a conventional wet process.

It is a still further object of this invention to provide a process for making strong, low basis weight, spontaneously dispersible sheets comprising modified cellulosic fibers.

Other objects will become apparent from a reading of the following Detailed Description of the Invention.

DETAILED DESCRIPTION OF THE INVENTION

This invention concerns strong, low basis weight, spontaneously dispersible sheets of modified cellulosic fibers. The sheets are strong in that they have adequate tensile strength and burst strength to be used in practical applications. The burst strength generally is greater than about 25 grams, preferably greater than about 100 grams. The basis weight of the sheets is from about 20 to about 250 grams per square meter, preferably from about 60 to about 180 grams per square meter. The density of the sheets is usually greater than about 0.20 gram per cubic centimeter.

As used herein, spontaneous dispersibility refers to that inherent characteristic of a sheet of fibers which results in the fibers becoming essentially completely separated one from another without the application of external forces when the sheet is placed in an essentially quiescent liquid. Unless otherwise indicated, the liquid is understood to be water.

In order to make the strong, low basis weight, spontaneously dispersible sheets (hereinafter fully compacted webs or products) of this invention, modified cellulosic fibers are first air laid. The moisture content of these air laid cellulosic fibers is then increased to from about 15% to about 40%. (Unless otherwise stated, all percentages herein refer to percent by weight of the fiberous structure.) The moisturized air laid fibers are then compressed. There is no necessity to dry the sheet so formed.

Fibers contemplated for use in this invention are those chemically modified cellulosic fibers which are sometimes known in the trade as super absorbent fibers. These fibers are, in general, characterized by an ability to internally absorb significant quantities of moisture, swelling greatly as they absorb this moisture. One characteristic fibers used in this invention must have is the ability to adsorb moisture, i.e. the ability to be wetted with a monomolecular layer over much of the interior surface of the fiber.

Fibers which are considered to be suitable for use in this invention include those described in U.S. Pat. Nos. 3,678,031 (Schoggen), dated July 18, 1972; 3,589,364 (Dean and Ferguson), dated June 29, 1971; 3,889,678 (Chatterjee and Schwenker) dated June 17, 1975; 2,639,239 (Elliott) dated May 19, 1953; 3,379,720 (Reid) dated Apr. 23, 1978; 3,936,441 (Holst et al.) dated Feb. 3, 1976; and Canadian Pat. No. 756,045 (Adams and Hoftiezer) dated Apr. 4, 1967.

Preferred for use in this invention are the super absorbent modified cellulosic fibers described by Dean and Ferguson in U.S. Pat. No. 3,589,364. These fibers, which are sometimes known as bibulous cellulosic fibers, are substantially water insoluble, wet cross-linked fibrous salts of sodium carboxymethylcellulose. A complete description of them is contained in the aforementioned patent to Dean and Ferguson, which patent is incorporated herein by reference.

Especially preferred for use in this invention are the super absorbent modified cellulosic fibers described by Schoggen in U.S. Pat. No. 3,678,031. These fibers are essentially acidic sodium carboxymethyl cellulose fibers. A complete description of them is contained in the aforementioned patent to Schoggen, which patent is incorporated herein by reference.

Mixtures of modified cellulosic fibers, such as, for example, mixtures in all proportions of bibulous cellulosic fibers and essentially acidic sodium carboxymethyl cellulose fibers, can be used in this invention.

Quantities of conventional wood pulp fibers (i.e. unmodified cellulosic fibers) can be included in admixture with the modified cellulosic. Any of the conventional fibers used in the preparation of paper products and absorbent airfelt products, such as communition grade wood pulp prepared from hardwoods and softwoods by conventional chemical (i.e. Kraft, sulfite, etc.) processes, and pulp prepared by chemi-mechanical, thermomechanical and mechanical pulping process can be used. These so-called conventional wood pulp fibers can be mixed with the modified cellulosic fibers at levels of pulp to about 75% by weight of total fiber.

Preferably, the fibers to be used in the practice of this invention are supplied in the form of dry lap sheets of the kind in common usage. Typically, such dry lap sheets have an air-dried basis weight of from about 450 to about 1600 grams per square meter.

The first step in the making of the strong, low basis weight, spontaneously dispersible product of this invention is the formation from the selected fibers of an air laid non-woven web, hereinafter called an airfelt. Any of the well known processes for forming airfelts can be used. In general, these processes involve supplying a dry lap sheet as hereinbefore described to a disintegrator such as that described in U.S. Pat. No. 3,825,194 which was issued to Buell on July 23, 1974. The dry lap sheet is separated by the disintegrator into individual fibers. These fibers are conveyed by air to a foraminous forming surface which can be any of those well known in the art, such as a wire screen. In a preferred embodiment of the instant invention, a low basis weight conveying tissue (sometimes called an envelope sheet or scrim), is placed on the foraminous forming surface. The conveying tissue serves as a means for maintaining the airfelt in a physically integral unit as it undergoes further processing. The conveying tissue will be stripped from the processed sheet at a later point in the process.

The Buell patent indicates that dry lap sheets having moisture levels less than about 10% are preferred for air laying. Those skilled in the art will readily appreciate the desirability of maintaining a low moisture level in the disintegrator so that the fibers are substantially completely separated one from the other and arrive in that condition at the foraminous forming surface. When the modified cellulosic fibers used in this invention are airlaid, the moisture content can be higher than that recommended by Buell because of the absorbent nature of the fibers. Moisture levels of up to about 15% to 18% are acceptable.

The airfelt should have a basis weight of from about 20 to about 250 grams per square meter, preferably from about 60 to about 180 grams per square meter.

Following formation of the airfelt, preferably on a conveying tissue, the moisture level of the airfelt must be adjusted to from about 15% to about 40%, preferably from about 15% to about 33%. Sheeted products can be formed from airfelts with moisture levels in excess of 33%, but such products are frequently wrinkled. Should the moisture level be significantly higher than 20%, the possibility of a need for a final drying step increases.

Without restricting the herein described invention in any manner, it is thought that an adsorbed layer of water molecules on the internal surfaces of the fibers is necessary for the proper operation of this invention. It can then be appreciated that water in the vapor state is highly useful in the practice of the invention.

Any technique which serves to increase the humidity of the atmosphere contacting the airfelt (i.e. any technique which increases the amount of water vapor contacting the airfelt) can be used to adjust the moisture level of the airfelt. For example, the technique can be as simple as passing high humidity air through the airfelt or exposing the airfelt to a high humidity atmosphere until the fibers reach the desired moisture level. Alternatively, the airfelt can be exposed to jets of saturated steam.

A third method by which the moisture level of the airfelt is increased to the requisite value involves the use of atomized sprays of water. Here, the airfelt is passed adjacent the atomizing spray head and the spray of atomized water is directed onto the airfelt. When this method is used, it is preferred that large drops of water be avoided since localized regions of excess liquid frequently result in puffed spots in the final product.

It should be noted that the hereinbefore described methods are techniques which provide areas of high humidity in the atmosphere contacting the airfelt. Any technique which accomplishes this result can be used.

Regardless of the type of moisturizing apparatus used, or the form in which the moisture is applied to the web, it is necessary that the moisture become essentially uniformly distributed throughout the airfelt. That is, a significant moisture gradient from the surface of the airfelt to its interior must not exist.

The process step following moisturization results in compaction of the moisturized airfelt. Compaction can be accomplished by any of the several techniques well known to those skilled in the art. Preferably, and most conveniently, compaction is accomplished by passing the moisturized web, with any associated conveying tissue, between a pair of opposed pressure-loaded rollers. The force applied to the rollers is typically from about 65 to about 450 kilograms per lineal centimeter of nip. Optionally, the pressure-loaded rollers can be heated. While the use of opposed pressure-loaded rollers is admirably suited to a continuous compaction process, should it be desirable to form the product of the invention in a batch-wise manner, the moisturized airfelt can be compacted between two planar members urged together by force exerting means such as, for example, hydraulic rams. Pressures of from about 10 to about 50 kilograms per square centimeter are preferred. As in the case of opposed pressure-loaded rollers, the planar members can optionally be heated.

Thus far, the process has been described in terms of a single moisturizing step and a single compaction step. While the fully compacted web of modified cellulosic fibers may be so obtained, it can also be produced by a series of alternatiing moisturizing and compaction steps. That is to say, some given fraction of the total moisture which is to be added to the airfelt (for example, 33% of the total moisture) is added to the airfelt by one of the methods described supra. The partially moisturized airfelt is then compacted as, for example, by being passed between a pair of opposed pressure-loaded rollers. A second increment of moisture is added to the now partially compacted airfelt and it is again compacted. A third increment of moisture is added, etc. Typically the moisture is added to the airfelt in three more or less equal increments prior to each of three compaction operations. As indicated supra, it is necessary that the moisture become essentially uniformly distributed throughout the airfelt prior to compaction.

When the process is operated in the immediately hereinbefore described alternating moisturizing-compaction mode, it is not necessary that each pair of pressure-loaded rollers be maintained at the same loading. While it is possible to operate the process with equal force loadings on each of the pairs of rollers, an acceptable product can be made if there is a force variation from one pair of pressure-loaded rollers to the next. The force loading on each pair of rollers preferably is in the range of from about 65 to about 150 kilograms per lineal centimeter of nip. The same general concept of variation of forces among the several compaction operations applies if techniques other than opposed pressure-loaded rollers are used.

When a conveying tissue is used, the moisture should be added to the airfelt, whether uncompacted or partially compacted, only on the surface opposite the conveying tissue. (Obviously, if the technique used to moisturize the airfelt is that of exposing the airfelt to an atmosphere with an elevated humidity, this limitation does not apply.) When the airfelt is sufficiently consolidated as, for example, after having passed through two or more moisturizing-compacting operations, and is sufficiently strong to be handled without the conveying tissue, the conveying tissue can optionally be stripped away. From this point forward through the process the airfelt may be moisturized by adding water to both sides of the partially compacted airfelt.

It is anticipated that the conveying tissue will be stripped from the compacted web of modified cellulosic fibers at some time prior to its ultimate use. Should the manufacturing process be operated in such a manner that the conveying tissue be still attached to the fully compacted web at the end of the manufacturing process, it is a mere matter of choice as to whether or not the conveying tissue is stripped away immediately following the ultimate compaction operation, at some point intermediate the ultimate compaction operation and delivery of the product to the ultimate user, or by the ultimate user at some point in its converting process. (It is possible, of course, that the ultimate user may find it advantageous to its own operation to retain the conveying tissue affixed to the fully compacted web of this invention; it is anticipated, however, that such will not be the usual situation.)

As noted supra, a final drying operation is unnecessary. If the amount of moisture added to the airfelt is controlled within the hereinbefore defined ranges, there will be no free moisture in the final product since the modified cellulosic fibers used in the invention are absorbent and can readily contain internally the moisture added during processing.

While the instant invention has been described with particularity in the foregoing paragraphs, it is believed that it may be better understood with the aid of the following examples. These appended examples are not intended to be exhaustive of the invention or its methods of practice; neither are they to be considered limitations to the invention.

EXAMPLE 1

Approximately 9.3 grams of the modified cellulosic fibers described by Dean and Ferguson in U.S. Pat. No. 3,589,364 (degree of substitution equal to about 0.7; epichlorohydrin cross-linked) were placed in a laboratory disintegrator and disintegrated, i.e. the individual fibers were separated one from another. The separated fibers were then airlaid onto a non-woven collection tissue to form a square airlaid web having 35.6 centimeter sides. At this point, the airlaid web had a moisture content of 15.1%. The airlaid web was cut into four square sections having sides 15.2 centimeters long.

One section of the airlaid web was placed on a wire mesh directly above a laboratory steam bath and subjected to essentially saturated steam at atmospheric pressure until the moisture content of the web was 21.9%. The moisturized web was then placed between two metal plates and subjected to a pressure of 7 kilograms force per square centimeter. After compaction, the web had a moisture content of 20.6% and a basis weight of 62 grams per square meter.

The sample was evaluated for burst strength and dispersibility characteristics.

In the dispersibility test, the sample is cut into 1.3 centimeter by 7.6 centimeter specimen strips. A specimen strip is placed over a glass hook and submerged into 30 milliliters of a test fluid contained in a petri dish. After 10 seconds, the glass hook is removed from the test liquid. A specimen strip strong enough to be removed from the test fluid by the hook is considered to have failed the dispersion test. A specimen strip which cannot be removed from the test fluid by the glass hook is considered to have passed the dispersion test. In the following tables, the letters "F" and "P" are used to note samples which fail and pass, respectively, the dispersion test. Generally, samples are evaluated in four test fluids: tap water ("water"), 0.1 N hydrochloric acid ("acid"), sodium hydroxide solution having a pH of 12 ("base"), and an aqueous methanol solution containing 50% by weight methanol ("methanol").

In the burst test, a 7.6 centimeter square sample is secured between two metal plates each having a 6.4 centimeter diameter circular orifice cut therein. The metal plates are aligned so that the circular orifices in each are in register. A rod provided with a 1.6 centimeter diameter spherical end is urged against that part of the sample exposed by the circular orifice in the metal plates. The force required to rupture the sample is denoted the burst strength of the sample. Usually, several specimens of the sample are evaluated for burst strength and the average of the results is reported.

Density of the fully compacted web is calculated by dividing the basis weight of the web by its thickness. Thickness is measured by means of a Model 13GW Ames Thickness Tester manufactured by the B. C. Ames Co., Waltham, Mass. Thickness is measured with a 141.7 gram force applied to the 4.1 centimeter diameter round anvil.

The results of the dispersion and burst tests conducted on the product of Example 1 were:

|  |  |
|---|---|
| Burst | 25.5 g. |
| Disintegration |  |
| Water | P |
| Acid | P |
| Base | P |
| Methanol | P |
| Density, $g/cm^3$ | 0.27 |

EXAMPLES 2 THROUGH 4

The procedure of Example 1 was followed, except that compaction pressures of 21.1, 35.2, and 46.9 kilograms per square centimeter were used. The results are shown in the following table.

|  | Ex. 2 | Ex. 3 | Ex. 4 |
|---|---|---|---|
| Pressure, $Kg/cm^2$ | 21.1 | 35.2 | 46.9 |
| Basis wt. $g/m^2$ | 63 | 58 | 63 |
| Moisture, % | 23 | 23 | 23 |
| Burst, g. | 92.3 | 121 | 151 |
| Disintegration |  |  |  |
| Water | P | P | P |
| Acid | P | P | P |
| Base | P | P | P |
| Methanol | P | P | P |
| Density, $g/cm^3$ | 0.41 | 0.46 | 0.55 |

The following experiments were conducted to show the effect of mixing unmodified cellulosic fibers with modified cellulosic fibers.

EXAMPLES 5 THROUGH 8

In these examples, the procedures of Examples 1 through 4 were followed except that the fibrous mixture was composed of 3 parts modified cellulosic fiber as used in Example 1 and 1 part unmodified cellulosic fiber. (The unmodified cellulosic fibers used in all the examples herein were mixed southern sulfate wood pulp fibers.)

|  | Ex. 5 | Ex. 6 | Ex. 7 | Ex. 8 |
|---|---|---|---|---|
| Pressure, $Kg/cm^2$ | 7.0 | 21.1 | 35.2 | 46.9 |
| Basis wt., $g/M^2$ | 58 | 56 | 66 | 55 |
| Moisture, % | 21.9 | 22.5 | 20.6 | 21.3 |
| Burst, g | 40 | 140 | 170 | 268 |
| Disintegration |  |  |  |  |
| Water | P | P | P | P |
| Acid | P | P | P | P |
| Base | F | P | P | P |
| Methanol | P | P | P | F |
| Density, $g/cm^3$ | 0.23 | 0.44 | 0.47 | 0.48 |

EXAMPLES 9 THROUGH 12

The procedures of Examples 1 through 4 were followed except that the fibrous mixture was comprised of 1 part modified cellulosic fiber and 1 part unmodified cellulosic fiber.

|  | Ex. 9 | Ex. 10 | Ex. 11 | Ex. 12 |
|---|---|---|---|---|
| Pressure, $Kg/cm^2$ | 7.0 | 21.1 | 35.2 | 46.9 |
| Basis wt., $g/M^2$ | 65 | 64 | 65 | 62 |
| Moisture, % | 20.6 | 21.3 | 20.6 | 21.3 |
| Burst, g | 112 | 296 | 520 | 483 |
| Disintegration |  |  |  |  |
| Water | P | P | P | P |
| Acid | P | P | F | P |
| Base | P | P | P | P |
| Methanol | F | F | F | F |
| Density, $g/cm^3$ | 0.30 | 0.42 | 0.47 | 0.49 |

EXAMPLES 13 THROUGH 16

The procedures used in Examples 1 through 4 were followed except the fibrous mixture was comprised of 1 part modified cellulosic fiber and 3 parts unmodified cellulosic fiber.

|  | Ex. 13 | Ex. 14 | Ex. 15 | Ex. 16 |
|---|---|---|---|---|
| Pressure, $Kg/cm^2$ | 7.0 | 21.1 | 35.2 | 46.9 |
| Basis wt., $g/M^2$ | 70 | 63 | 64 | 74 |
| Moisture, % | 18.7 | 19.3 | 18.7 | 18.0 |
| Burst, g | 200 | 299 | 298 | 486 |
| Disintegration |  |  |  |  |
| Water | P | P | P | P |
| Acid | F | F | F | F |
| Base | P | P | P | F |
| Methanol | F | F | F | F |
| Density, $g/cm^3$ | 0.25 | 0.35 | 0.42 | 0.48 |

EXAMPLES 17 THROUGH 20

The procedures used in Examples 1 through 4 were followed except the fibers were unmodified cellulosic fibers. These examples represent the controls against which the foregoing examples may be compared.

|  | Ex. 17 | Ex. 18 | Ex. 19 | Ex. 20 |
|---|---|---|---|---|
| Pressure, $Kg/cm^2$ | 7.0 | 21.1 | 35.2 | 46.9 |
| Basis wt., $g/M^2$ | 61 | 69 | 66 | 64 |
| Moisture, % | 20.0 | 18.0 | 17.3 | 20.6 |
| Burst, g | 37 | 64 | 91 | 63 |
| Disintegration |  |  |  |  |
| Water | F | F | F | F |
| Acid | F | F | F | F |
| Base | F | F | F | F |
| Methanol | F | F | F | F |

-continued

|  | Ex. 17 | Ex. 18 | Ex. 19 | Ex. 20 |
|---|---|---|---|---|
| Density, g/cm$^3$ | 0.22 | 0.34 | 0.40 | 0.46 |

EXAMPLES 21 THROUGH 23

Modified cellulosic fibers as used in Examples 1 through 16 were disintegrated and continuously airlaid onto a moving collection tissue at a basis weight of approximately 90 grams per square meter. The airlaid web was then subjected to stepwise humidification and compaction. Humidification was provided by nozzles located adjacent the moving airfelt web and in which water and air were mixed so as to provide a light moisturizing spray. The moisturized web was then passed between two opposed pressurized rollers. A total of three moisturizing and three compaction steps was used. During the first two moisturizing steps, the atomizing heads were located only adjacent the upper surface of the airlaid pad. Following the second compaction step, the conveying tissue on the bottom of the airlaid web was stripped away. The third moisturizing step involved the passage of the web adjacent moisturizing nozzles above and below the web. In the following table, Example 21 represents the sample after one moisturizing and compaction operation. Example 22 represents the sample after two moisturizing and compaction steps, and Example 23 represents the sample after three moisturizing and compaction steps. As used in the following table, "moisture" refers to the total amount of moisture, in grams, added to one gram of fiber in the airlaid web.

|  | Ex. 21 | Ex. 22 | Ex. 23 |
|---|---|---|---|
| Pressure, Kg/cm | 119 | 119 | 119 |
| Basis wt., g/M$^2$ | 90 | 90 | 90 |
| Moisture, g/g | 0.121 | 0.144 | 0.617 |
| Burst | 100 | 424 | 767 |
| Disintegration |  |  |  |
| Water | P | P | P |
| Acid | P | P | P |
| Base | P | P | P |
| Methanol | F | F | F |
| Density, g/cm$^3$ | 0.32 | — | 0.61 |

EXAMPLE 24

The procedures used in Examples 21 through 23 are repeated except that different modified cellulosic fibers are used. Essentially acid sodium carboxymethyl cellulose fibers, as described by Schoggen in U.S. Pat. No. 3,678,031, having a degree of substitution between 0.7 and 0.9, water retention value and salt retention value (as defined in the Schoggen patent), of, respectively, from about 2,000 to about 4,000 and from about 1,000 to about 1,500 are used in this example. A fully compacted web having good strength and spontaneous dispersibility in water is produced.

EXAMPLE 25

Modified cellulosic fibers as used in Example 24 air airlaid to form an airfelt by disintegrating dry lap sheets of the fibers, conveying the essentially completely separated fibers with a stream of dry air from the disintegrator to a forming zone, and forming an airfelt having a basis weight of 100 grams per square meter on a nonwoven conveying tissue. Air is conditioned to 20° C. and 85% relative humidity in a humidification chamber by independently heating the air and spraying atomized water into the chamber. Dry bulb and wet bulb temperatures are monitored to control the temperature and relative humidity of the air. The air thus conditioned is passed at a rate of 74 cubic meters of conditioned air per minute per square meter of airfelt through the previously formed airfelt for an average time of 160 seconds. The moisturized airfelt is compacted by being passed between a pair of opposed rollers loaded to a pressure of from about 89 to about 178 kilograms force per centimeter of nip. The resulting product is strong and spontaneously dispersible in water.

INDUSTRIAL APPLICABILITY

The fully compacted webs of this invention can be used as absorbent elements in disposable products such as diapers, sanitary napkins, catamenial tampons, incontinent pads, and the like. They can also be used as vehicles for the delivery of biologically active materials to humans and animals and for the delivery of insecticides and growth regulators to plants. They can be used as the active element in products designed to remove essentially all the undissolved water from substantially immiscible aqueous systems comprised of water together with at least one organic material such as a hydrocarbon and the like. In general, the products of this invention can be used in any application requiring that modified cellulosic fibers be presented in the form of strong, low basis weight, spontaneously dispersible sheets.

What is claimed is:

1. A process for making a strong, spontaneously dispersible sheet of modified cellulosic fibers comprising the steps of:
   (a) airlaying modified cellulosic fibers to form a substantially uniform nonwoven airfelt web having a basis weight of about 20 to about 250 grams per square meter, said fibers having the ability to be wetted with a monomolecular layer of water over significant portions of the interior surface thereof;
   (b) adjusting the moisture content of said formal web at least once to provide said web with a substantially uniform distribution of moisture and to attain a moisture content of about 15 to about 40% by weight; and
   (c) pressing said web at least once sufficiently to bond together said fibers into a strong, spontaneously dispersible, unitary sheet of said modified cellulosic fibers.

2. The process of claim 1 wherein said pressing step is accomplished by the use of at least one pair of opposed pressure loaded rollers wherein the force applied to each pair of said opposed pressure loaded rollers is from about 65 to about 450 kilograms per lineal centimeter of nip.

3. The process of claim 1 wherein said pressing step is accomplished by the use of two planar members urged together by force exerting means and wherein the pressure applied to said planar members is from about 10 to about 50 kilograms per square centimeter.

4. The process of claim 1 wherein said web has a basis weight of about 60 to about 180 grams per square meter and the moisture content of said web is adjusted to about 15 to about 33% by weight.

5. The process of claim 4 wherein said pressing step is accomplished by the use of at least one pair of opposed pressure loaded rollers wherein the force applied to each pair of said opposed pressure loaded rollers is from about 65 to about 450 kilograms per lineal centimeter of nip.

6. The process of claim 4 wherein said pressing step is accomplished by the use of two planar members urged together by force exerting means and wherein the pressure applied to said planar members if from about 10 to about 50 kilograms per square centimeter.

7. The process of claim 1, 2, 3, 4, 5, or 6 wherein said modified cellulosic fibers are selected from the group consisting of:
(i) bibulous cellulosic fibers;
(ii) essentially acidic sodium carboxymethyl cellulose fibers; and
(iii) mixtures thereof.

8. The process of claim 1, 2, 3, 4, 5 or 6 wherein said modified cellulosic fibers are airlaid on a conveying tissue.

9. The process of claim 1, 2, 3, 4, 5, or 6 wherein said pressing step is followed by at least one pair of additional processing steps wherein said steps comprise:
(A) adjusting the moisture content of said web to about 15% to about 40% by weight; and
(B) pressing said web.

10. The process of claim 1, 2, 3, 4, 5 or 6 wherein said modified cellulosic fibers are selected from the group consisting of:
(i) bibulous cellulosic fibers;
(ii) essentially acidic sodium carboxymethyl cellulose fibers; and
(iii) mixtures thereof; and
wherein said fibers are airlaid on a conveying tissue; and wherein said pressing step is followed by at least one pair of additional processing steps wherein said steps comprise:
(A) adjusting the moisture content of said web to about 15 to about 40% by weight; and
(B) pressing said web.

11. A process for making a strong, spontaneously dispersible sheet of bibulous cellulosic fibers comprising:
(a) continuously airlaying said bibulous cellulosic fibers to form a substantially uniform nonwoven airfelt web having a basis weight of about 60 to about 180 grams per square meter;
(b) adjusting the moisture content of said web about 15 to about 33% by weight; and
(c) continuously pressing said web sufficiently to bond together said fibers into a strong, spontaneously dispersible unitary sheet by passing said web between at least one pair of opposed pressure loaded rollers subjected to a force of about 65 to about 150 kilograms per lineal centimeter of nip.

12. A process for making a strong, spontaneously dispersible sheet of essentially acidic sodium carboxymethyl cellulose fibers comprising:
(a) continuously airlaying said essentially acidic carboxymethyl cellulose fibers to form a substantially uniform nonwoven airfelt web having a basis weight of about 60 to about 180 grams per square meter;
(b) adjusting the moisture content of said web to provide said web with a substantially uniform distribution of moisture and to attain a moisture content of about 15 to about 33% by weight; and
(c) continuously pressing said web sufficiently to bond together said fibers into a strong, spontaneously dispersible unitary sheet by passing said web between at least one pair of opposed pressure loaded rollers subjected to a force of about 65 to about 150 kilograms per lineal centimeter of nip.

* * * * *

UNITED STATES PATENT AND TRADEMARK OFFICE
CERTIFICATE OF CORRECTION

PATENT NO. : 4,252,761
DATED : February 24, 1981
INVENTOR(S) : HOWARD L. SCHOGGEN and JOHN W. SMITH It is certified that error appears in the above-identified patent and that said Letters Patent are hereby corrected as shown below:

Column 5, line 27, "alternatiing" should read --alternating--.

Column 6, line 24-25, "absorbent" should read --adsorbent--.

Column 9, line 61, "air" should read --are--.

Column 11, line 7, "if" should read --is--.

Signed and Sealed this

Nineteenth Day of May 1981

[SEAL]

Attest:

RENE D. TEGTMEYER

Attesting Officer

Acting Commissioner of Patents and Trademarks